US00PP26517P3

(12) United States Plant Patent
Corgan

(10) Patent No.: US PP26,517 P3
(45) Date of Patent: Mar. 15, 2016

(54) *CANNA* PLANT NAMED 'FIRE DRAGON'

(50) Latin Name: *Canna×generalis*
Varietal Denomination: Fire Dragon

(71) Applicant: Joe Corgan, Las Cruces, NM (US)

(72) Inventor: Joe Corgan, Las Cruces, NM (US)

( * ) Notice: Subject to any disclaimer, the term of this patent is extended or adjusted under 35 U.S.C. 154(b) by 122 days.

(21) Appl. No.: 14/120,554

(22) Filed: Jun. 3, 2014

(65) Prior Publication Data

US 2015/0351306 P1 Dec. 3, 2015

(51) Int. Cl.
*A01H 5/00* (2006.01)

(52) U.S. Cl.
USPC ..... Plt./415

(58) Field of Classification Search
USPC ..... Plt./415
See application file for complete search history.

*Primary Examiner* — Annette Para
(74) *Attorney, Agent, or Firm* — Bethany R. Roahrig; James M. Weatherly; Cochran Freund & Young, LLC

(57) ABSTRACT

A new and distinct cultivar of *Canna* plant named 'Fire Dragon' that is characterized by a semi-dwarf habit, mid-green foliage, and pure scarlet flowers which are open faced, long-lived, self-cleaning, and attractively arranged within the inflorescence, is disclosed

2 Drawing Sheets

Genus and species: *Canna×generalis.*
Variety denomination: 'Fire Dragon'.

BACKGROUND OF THE NEW PLANT

The present invention relates to a new and distinct cultivar of *Canna*, also known as *Canna* Lily or Indian Shot, which is grown as an ornamental annual or perennial, according to climate zone, for use in planted containers and in the garden and landscape. The new cultivar is known botanically as *Canna×generalis*, and will be referred to hereinafter by the cultivar name 'Fire Dragon'.

A *Canna* breeding program was carried out in Las Cruces, N. Mex. since 1996. The aim of the breeding program is to develop new dwarf or semi-dwarf *canna* varieties in various flower colors and foliage colors, with well-formed inflorescences consisting of flowers which are self-cleaning.

'Fire Dragon' arose and was selected in 2002 as an open-pollinated seedling whose male parent is unknown and whose female parent is *Canna* 'The President' (unpatented). The open-pollination was conducted on the inventor's property in Las Cruces, N. Mex.

'Fire Dragon' was first asexually reproduced in Las Cruces, N. Mex. in 2002. Asexual propagation was accomplished by division of the rhizome. Since that time, under careful observation, the distinguishing characteristics of 'Fire Dragon' have been determined stable and uniform, and to reproduce true to type in successive generations of asexual propagation via division of the rhizome.

SUMMARY

The distinguishing characteristics of 'Fire Dragon' are as follows. 'Fire Dragon' has not been tested under all possible conditions and phenotypic differences may be observed with variations in environmental, climatic, and cultural conditions.

1. 'Fire Dragon' is semi-dwarf, achieving a height 75 cm to 90 cm in one year of growth in a 2-gallon container, and 120 cm to 150 cm as a mature plant in the ground.

2. 'Fire Dragon' exhibits early basal branching, giving rise to a fuller display in containers and in the landscape.
3. The foliage of 'Fire Dragon' is mid-green in color.
4. The inflorescence of 'Fire Dragon' are scarlet in color, without any other coloration present in any part of the inflorescence.
5. Each flower (actually, staminode cluster) of 'Fire Dragon' is long-lived, remaining attached to the inflorescence for 7 to 10 days.
6. The old flowers of 'Fire Dragon' fall away from the inflorescence without lodging within, that is, the flowers are self-cleaning.
7. The inflorescence of 'Fire Dragon' becomes large and showy, consisting of 8 to 10 open flowers before the oldest flower falls away.
8. The flowers of 'Fire Dragon' are open faced and attractively arranged within the inflorescence.

DESCRIPTION OF THE PHOTOGRAPHS

The accompanying color photographs illustrate the overall appearance of 'Fire Dragon' showing the color of the inflorescence and the foliage as true as it is reasonably possible to obtain in colored reproductions of this type. Both photographs were taken in April 2014.

Figure 1:
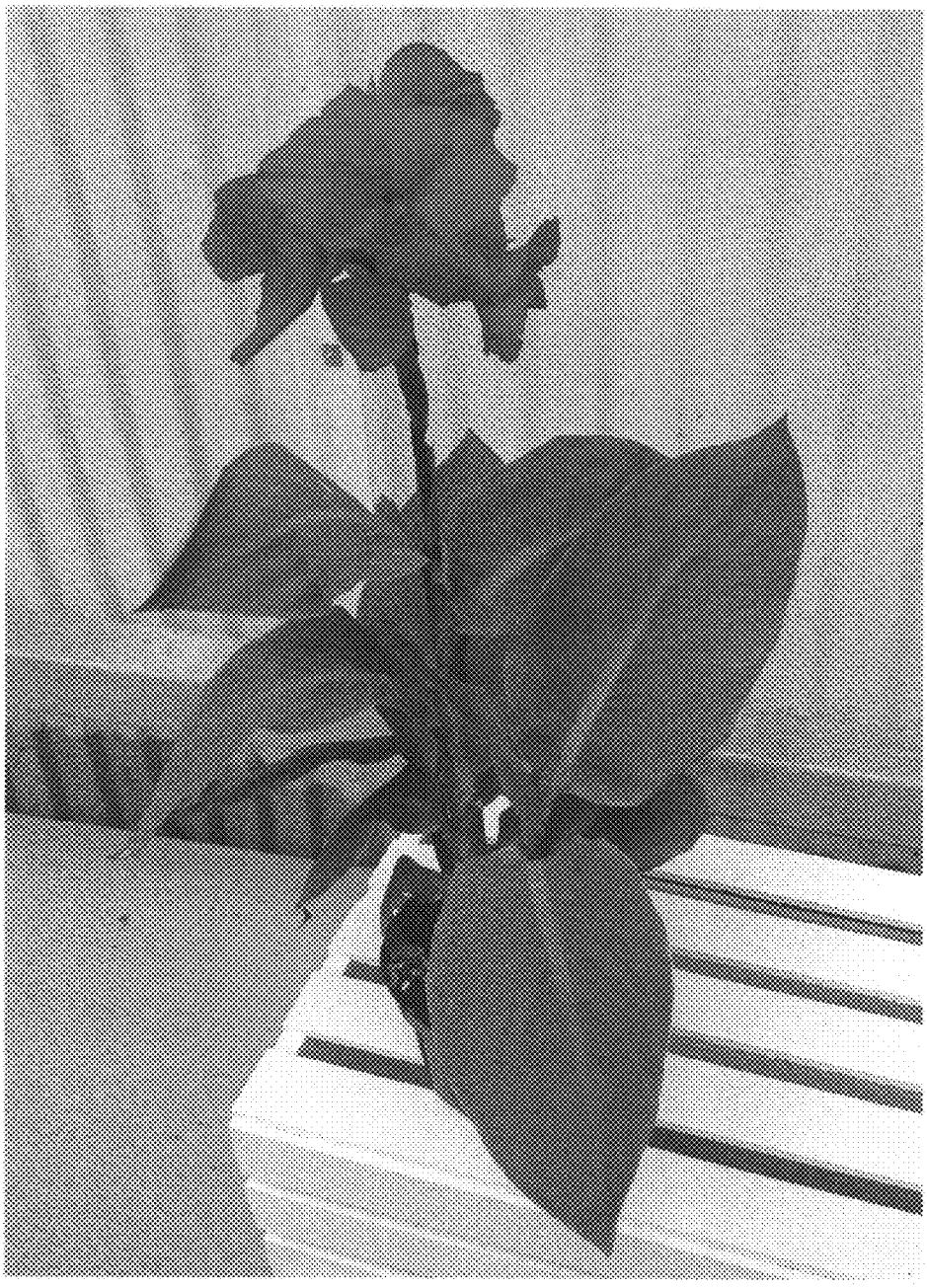

FIG. 1 depicts a nine-month old plant of 'Fire Dragon' which has been grown in a 2-gallon container outdoors in Oxnard, Calif. The plant has been grown without any chemical growth retardant. This photograph shows the early basal branching of 'Fire Dragon'.

Figure 2:
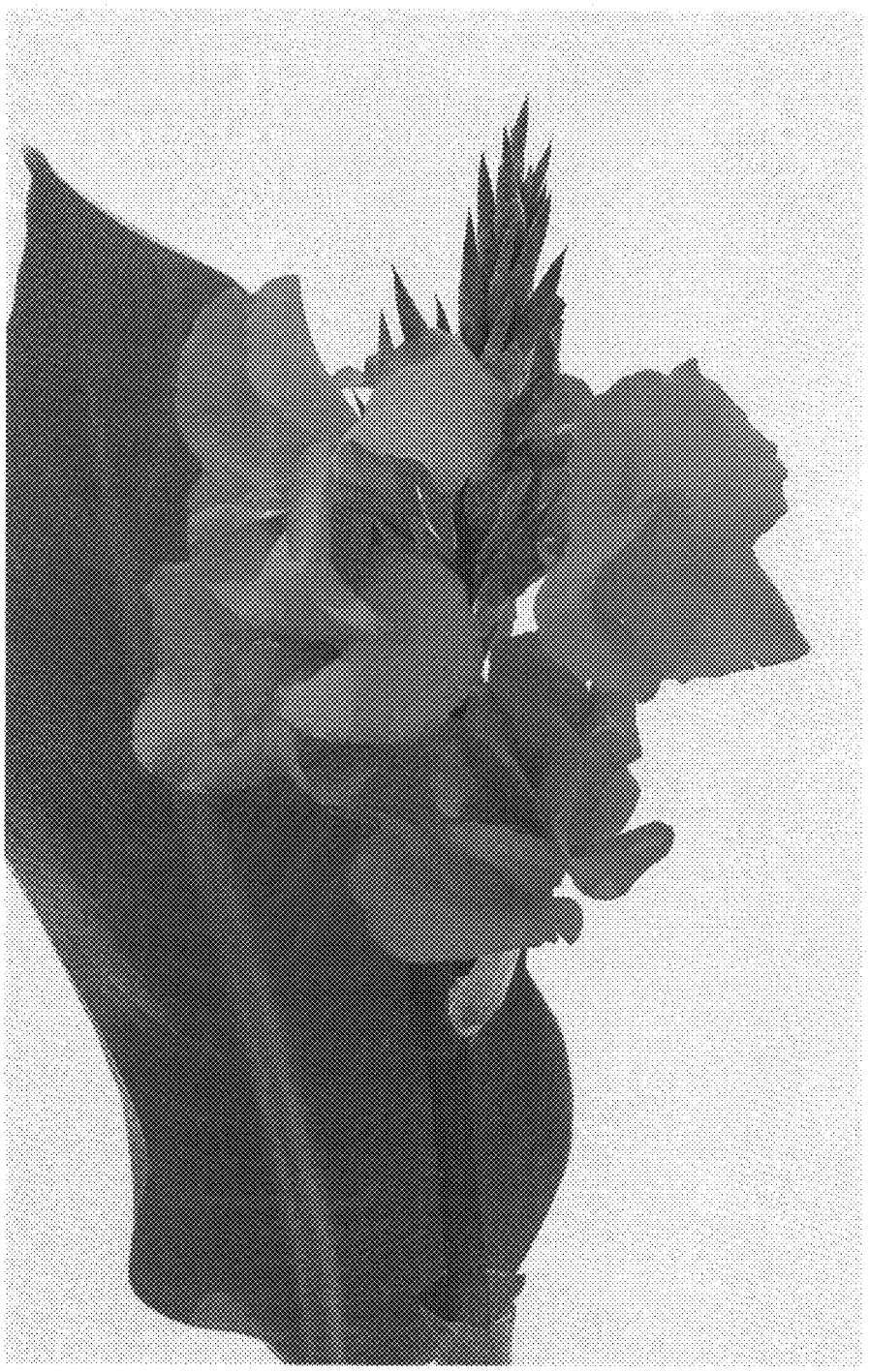

FIG. 2 depicts a close-up view of the inflorescence of 'Fire Dragon'. In this photograph, six flowers (actually staminodes) are fully developed with approximately twelve further buds in various stages of development.

DESCRIPTION OF THE NEW VARIETY

In the following botanical description, all color references are made to The Royal Horticultural Society Colour Chart, 2007 Edition, except where general terms of ordinary dictionary significance are used.

The plant used for this botanical description was five-months old from a tissue cultured division and had been grown in a 2-gallon container outdoors in Oxnard, Calif. Botanical descriptions were taken in April 2014.

Botanical classification: *Genus and species.*—*Canna*×*generalis.*

Parentage: Open-pollination between an unknown male parent and *Canna* 'The President' (unpatented) as female parent.

Plant:

*Propagation*.—By division of field-grown rhizomes or by division of tissue cultured plants.

*Cultural suggestions*.—In common with *Cannas* generally, 'Fire Dragon' is evergreen in warm climates, but will die back as winter approaches in cool climates. Rhizomes may be mulched to protect from light frost but should be lifted and stored if the ground is liable to freeze below the surface.

*Hardiness*.—'Fire Dragon' is hardy and evergreen in USDA Zone 8.

*Heat tolerance*.—Plants grow and flower rapidly in sunny positions.

*Pest and disease resistance or susceptibility*.—'Fire Dragon' has not been found to be more or less resistant or susceptible to the pests and diseases which affect the genus and its cultivars, of which *Canna* yellow mosaic virus, *Canna* yellow streak virus and *Canna* yellow mottle virus are endemic in many *Canna* plants in the landscape.

*Plant form*.—Upright with one or more basal branch shoots.

*Rhizome description*.—Thick, fibrous, 3 cm to 5 cm in diameter, with papery scales which are light brown 166C in color when first forming, becoming dark brown 200B as they age and peel away from the rhizome whose revealed surface is smooth, cream 11D.

*Plant height after one year in a 2-gallon container.*—75 cm to 90 cm (including inflorescence).

*Plant spread.*—40 cm to 50 cm.

Stem (each basal shoot, to base of inflorescence):

*Length.*—35 cm to 45 cm.

*Diameter.*—1.5 cm.

*Internode length.*—7 cm to 12 cm.

*Stem strength*.—The stem is firm and fleshy towards base, becoming very hard and stiff towards the inflorescence.

*Texture*.—Slightly rough with longitudinal ribs towards base, smooth towards inflorescence.

*Color.*—144C at the base, N79A above the highest leaf.

Foliage:

*Form*.—Simple and entire.

*Leaf arrangement*.—Alternate.

*Leaf length.*—30 cm to 32 cm.

*Leaf width.*—14 cm to 17 cm.

*Shape*.—Ovate.

*Apex*.—Acute.

*Base*.—Obtuse.

*Margin*.—Entire.

*Surface texture* (*both surface*).—Glabrous.

*Leaf structure*.—Leaf is supported by a stiff depressed midrib and by raised parallel lateral ribs which are spaced approximately 1 cm apart.

*Venation*.—Pinnate.

*Vein color* (*both surfaces*).—138B.

*Leaf color* (*both surfaces*).—138A.

*Petioles*.—Arrangement: Sheathing. Length: 10 cm. Texture: Glabrous, ribbed. Color, upper surface: 144C. Color, lower surface: 144C becoming 59C where petiole is exposed to full sun.

Inflorescence:

*Form*.—Terminal raceme consisting of 14 to 18 flowers.

*Height* (*fully developed*).—25 cm to 30 cm.

*Diameter* (*fully developed*).—20 cm.

*Bract*.—Raceme is subtended by single paper-like bract.

*Bract shape*.—Cymbiform.

*Bract dimensions.*—9 cm in length, 2.5 cm in width.

*Bract color*.—Adaxial surface 59C, abaxial surface N144A.

*Peduncle*.—Dimensions: 12 cm in length, 1.0 cm in diameter. Strength: Hard and very stiff. Texture: Glabrous. Color: N79A.

Flower:

*Overall description*.—Flower is complex, comprised of three short bracteoles subtending calyx of three short waxy sepals and three narrow petals. The showy elements of the flower are modified petaloid stamens or staminodes of which three outer staminodes are large and wide, and a fourth is narrow and recurving (labellum). A fifth (inner) staminode bears a lone marginal anther and is adjacent to a long slender petaloid style.

*Natural flowering season*.—Continually from late spring until fall.

*Flower longevity on the plant.*—7 to 10 days.

*Flower fragrance*.—None.

*Flower dimensions.*—5.5 cm in height, 8 cm to 9 cm in width.

*Pedicels*.—Dimensions: 0.8 cm in length, 0.4 cm in diameter. Texture: Glabrous. Color: N79A.

*Buds*.—Dimensions: 4 cm in length, 0.6 cm in width. Shape: Ellipsoid. Surface: Smooth, appears slightly farinaceous. Color: 46A.

*Bracteoles*.—Number: 3, fused at base. Dimensions: 10 mm in length, 5 mm in width. Shape: Elliptic, apex acute, base truncate. Color: Adaxial surface 46A, abaxial surface 50B. Surface, texture: Glossy, waxy.

*Sepals*.—Number: 3, fused at base. Dimensions: 18 mm in length, 9 mm in width. Shape: Elliptic, apex acute, base truncate. Color: Adaxial surface 46A, abaxial surface 50B. Surface texture: Farinaceous, waxy.

*Petals*.—Number: 3, fused at base. Dimensions: 4.5 cm to 5.5 cm in length, 13 mm in width. Shape: Elongate elliptic, apex acute, base truncate. Margin: Smooth, entire. Color (both surfaces): 46A. Surface: Glabrous.

*Outer staminodes*.—Number: 4, fused at base. Shape, dimensions: 3 staminodes broad obovate, apex round, base truncate, 8 cm in length, 6.5 cm in width; 1 staminode (labellum) spatulate, recurving, 8 cm in length, 3.5 cm in width. Margin: Smooth, entire, undulating. Color (both surfaces): 45B. Surface: Glabrous.

*Inner staminode* (*anther bearing*).—Shape: Spatulate, apex round, base truncate. Dimensions: 6.0 cm to 6.5 cm in length, 1.5 cm in width. Margin: Smooth, entire. Color (both surfaces): 45B. Surface: Glabrous.

*Inner petaloid style*.—Shape: Falcate, apex truncate, base truncate. Dimensions: 6.0 cm in length, 5 mm in width. Margin: Smooth, entire. Color (both surfaces): 45B. Surface: Glabrous.

Reproductive organs:

*Stamens.*—1 petaloid anther-bearing staminode as above.

*Anthers.*—Not always present; where present, fused along half anther length to concave margin of staminode.

*Anther shape.*—Rectangular.

*Anther dimensions.*—Length 12 mm, width 1.5 mm.

*Color.*—161A.

*Pollen amount.*—Slight, appears to transfer to style before flower opens.

*Pollen color.*—161A.

*Style, stigma.*—1 petaloid style as above; stigma absent.

*Ovary.*—Inferior, 3-carpellate, surface rough with many tiny pinhead-like protrusions, color 59B.

Seed: Seed has not been observed.

COMPARISON TO PARENTAL VARIETY AND COMMERCIAL VARIETY

The variety of *Canna* which is considered by the inventor to most closely resemble 'Fire Dragon' is the female parent plant, *Canna* 'The President' (unpatented). In comparison, the flowers of 'Fire Dragon' are self-cleaning, while the old flowers of 'The President' remain held within the inflorescence. In addition, the flowers of 'Fire Dragon' are entirely scarlet in color, whereas the flowers of 'The President' exhibit a yellow ribbon effect along the staminode margins together with an orange throat or staminode bases.

Three other varieties of red-flowered *Canna* are known to the inventor and may be compared as follows. *Canna* 'Red King Humbert' bears pure scarlet flowers on bronze-purple foliage. The two varieties *Canna* 'South Pacific Scarlet' and *Canna* 'Tropical Red' are raised from seed and exhibit red flowers with evident orange throats or staminode bases. The flowers of 'Fire Dragon' are entirely scarlet in color with mid-green colored foliage.

I claim:

1. A new and distinct variety of *Canna* plant named 'Fire Dragon' as shown and described herein.

* * * * *